United States Patent [19]

Bowman et al.

[11] Patent Number: 5,030,740

[45] Date of Patent: Jul. 9, 1991

[54] PROCESS FOR PREPARING LINEARLY-EXTENDED POLYALKYLENEPOLYAMINES

[75] Inventors: Robert G. Bowman; David C. Molzahn; George E. Hartwell, all of Midland, Mich.

[73] Assignee: The Dow Chemical Company, Midland, Mich.

[21] Appl. No.: 257,891

[22] Filed: Oct. 14, 1988

[51] Int. Cl.[5] .................. C07C 209/16; C07D 403/14
[52] U.S. Cl. ..................................... 544/357; 564/480
[58] Field of Search ........................ 544/357; 564/480

[56] References Cited

U.S. PATENT DOCUMENTS

| | | | |
|---|---|---|---|
| 1,875,746 | 9/1932 | Martin et al. | |
| 2,082,105 | 6/1937 | Herold et al. | 260/127 |
| 3,231,616 | 7/1966 | Jones | 260/581 |
| 3,270,059 | 8/1966 | Winderl et al. | 260/583 |
| 3,272,865 | 9/1966 | Barker | 260/581 |
| 3,364,218 | 1/1968 | Brader | 260/268 |
| 3,475,344 | 10/1969 | Adam et al. | 252/432 |
| 3,491,148 | 1/1970 | Winderl et al. | 260/563 |
| 3,714,259 | 1/1973 | Lichtenwalter et al. | 260/583 P |
| 3,875,235 | 4/1975 | Noeske et al. | 260/585 B |
| 4,206,150 | 6/1980 | Slaugh | 260/583 R |
| 4,217,240 | 8/1980 | Bergna | 252/313 S |
| 4,233,139 | 1/1980 | Murrell et al. | 208/112 |
| 4,404,399 | 9/1983 | Kochar et al. | 564/402 |
| 4,495,369 | 1/1985 | Werner et al. | 564/480 |
| 4,552,961 | 11/1985 | Herdle | 564/480 |
| 4,613,705 | 9/1986 | Hargis | 564/409 |
| 4,683,335 | 7/1987 | Knifton et al. | 564/480 |

FOREIGN PATENT DOCUMENTS 48-96475 12/1973 Japan.
55-53250 4/1980 Japan.
58-35179 3/1983 Japan.

OTHER PUBLICATIONS

"[17]O Nuclear Magnetic Resonance Spectroscopy of Polyoxometalates", by M. Filowitz, R. K. C. Ho, W. G. Klemperer and W. Shum, Inorganic Chemistry, 18 (1979), 93-103.
"Niobotungstic Acid $Nb_2W_4O_{19}H$, Its Anhydride, and its Alkyl/Silyl Esters", V. W. Day, W. G. Klemperer and C. Schwartz, Journal of the American Chemical Society, 109 (1987), 6030-6044.
Unverified Translation of Japanese 48-96475.
Unvarified Translation of Japanese 83-35179.
Abstract of Japanese 53,250 of 10/16/78.

Primary Examiner—Robert Gerstl
Attorney, Agent, or Firm—Michael S. Jenkins

[57] ABSTRACT

A process for preparing linearly-extended polyalkylenepolyamines, such as linear and branched polyethylenepolyamines, comprising contacting a difunctional aliphatic alcohol, such as monoethanolamine, with a reactant amine, such as ethylenediamine, in the presence of a catalyst containing tungsten oxide essentially free of the metals of Groups VIII, IB, and IIB of the Periodic Table. Included among the linearly-extended polyalkylenepolyamines are alcohol-extended piperazines, such as N-(2-hydroxyethyl)-piperazine, and amine-extended piperazines, such as N-(2-aminoethyl)-piperazine.

33 Claims, No Drawings

PROCESS FOR PREPARING LINEARLY-EXTENDED POLYALKYLENEPOLYAMINES

BACKGROUND OF THE INVENTION

This invention relates to a process for preparing linearly-extended polyalkylenepolyamines, such as diethylenetriamine and linear and branched triethylenetetramines. Linearly-extended polyalkylenepolyamines also include alcohol-extended piperazines, such as N-(2-hydroxyethyl)piperazine, and amine-extended piperazines, such as N-(2-aminoethyl)-piperazine.

Linearly-extended polyalkylenepolyamines find utility as dispersants, surfactants, chelants, catalysts, curing agents, and extenders in polyurethanes. In addition, linearly-extended polyalkylenepolyamines are useful starting materials or intermediates in the preparation of pesticides, veterinary antihelmintic pharmaceuticals, and high temperature lubricating oils.

It is known that non-cyclic polyalkylenepolyamines can be prepared by the reaction of an alkyl halide with ammonia or an amine. The product is a polyalkylenepolyamine hydrohalide salt, which must be neutralized with base in order to recover the valuable polyalkylenepolyamine product. The neutralization produces a waste stream of metal salt, which must be removed. Moreover, the process produces considerable amounts of undesirable cyclic compounds.

It is known that salt-free linear polyethylenepolyamines can be prepared directly by reacting an ethanolamine with an ethyleneamine in the presence of hydrogen and a hydrogenation catalyst. For example, U.S. Pat. No. 3,714,259 discloses such a process with preferred catalysts derived from the oxides of chromium, copper, nickel, and cobalt. Likewise, U.S. Pat. No. 3,270,059 teaches a process for production of diaminoalkanes comprising passing a mixture of alkanediols or alkanolamines, ammonia, and hydrogen over a catalyst containing at least one metal sensitive to sulfur or sulfur compounds. Preferably, the metal is a metal from Groups IB or VIII, including copper, silver, iron, nickel and cobalt. Optionally, promoters such as compounds of Group VIB elements can be employed. These processes produce substantial quantities of undesirable cyclic products, such as piperazine. Moreover, these catalysts require large amounts of hydrogen to maintain the catalytic activity.

U.S. Pat. No. 4,206,150 teaches the amination of aliphatic diols with ammonia or primary or secondary amines, preferably, containing one amine group. The process is conducted in the presence of a catalyst containing a mixture of components selected from the group consisting of copper, copper oxide, and mixtures thereof, and molybdenum oxide, tungsten oxide, and mixtures thereof. This process requires on a mole basis more copper than molybdenum or tungsten, and favors use of hydrogen to maintain the catalyst's activity.

It would be advantageous to have a process for the direct amination of aliphatic alcohols to polyalkylenepolyamines which does not require large amounts of hydrogen and expensive metals. It would be more advantageous if such a process produces high selectivity for linearly-extended products and low selectivity for undesirable cyclic materials. It would be most advantageous if the catalyst for such a process is insoluble in the presence of amines and retains its physical integrity in the presence of water. Such a process would eliminate the need for neutralizing hydrohalide salts and disposing of a waste salt stream. Moreover, in such a process the problems of catalyst leaching, reactor plugging, and catalyst separation would be avoided. Accordingly, the combined aforementioned advantages would render the amination process suitable for industrial applications.

SUMMARY OF THE INVENTION

In one aspect this invention is a process for preparing linearly-extended polyalkylenepolyamines which comprises contacting a difunctional aliphatic alcohol with a reactant amine in the presence of a catalyst, described hereinafter. The contacting is conducted under reaction conditions such that a mixture of polyalkylenepolyamines enriched in linearly-extended products is produced. For the purposes of this invention "linearly-extended products" are defined as amine products arising from the condensation of the difunctional aliphatic alcohol and amine reactants. Linearly-extended products are to be distinguished from undesirable cyclic products, which arise when the condensation of the alcohol and amine reactants is followed by internal cyclization to form an undesirable nitrogen-containing heterocycle.

The catalyst employed in the process of this invention contains tungsten oxide which is essentially free of metals selected from Groups VIII, IB, and IIB of the Periodic Table. The term "essentially free" means that each Group VIII, IB, or IIB metal is present in the tungsten oxide catalyst at a concentration less than about 0.1 weight percent.

Advantageously, the process of this invention is direct, so that there is no need to neutralize a hydrohalide salt and eliminate a metal salt waste stream. More advantageously, the process of this invention does not require hydrogen. Even more advantageously, the process of this invention is capable of achieving high yields of valuable linearly-extended polyalkylenepolyamines and low yields of undesirable cyclic products. Most advantageously, the catalyst of this invention is insoluble in liquid amines and water; therefore, catalyst losses are minimized and the separation of products from the catalyst is relatively easy. Consequently, the process of this invention is suitable for industrial use.

The linearly-extended polyalkylenepolyamine products of this invention are useful as dispersants, surfactants, chelants, curing agents, and catalysts, and useful in the formation of urethane polymers, ureas, pesticides, and antihelmintic pharmaceutical products.

In another aspect this invention is a catalyst composition comprising a multinuclear tungsten oxide compound supported on a refractory oxide. Said catalyst composition is useful in the amination process, described hereinbefore.

DETAILED DESCRIPTION OF THE INVENTION

The difunctional aliphatic alcohols which are employed in the process of this invention include any aliphatic alcohol containing (a) at least one hydroxyl moiety bound to a primary carbon atom, and (b) at least one additional moiety selected from the group consisting of hydroxyl, primary amine and secondary amine functionalities. Examples of suitable difunctional alcohols include diols such as ethylene glycol and propylene glycol, triols such as glycerol, and higher polyols; polyether polyols such as diethylene glycol, ethylene oxide-capped polypropylene glycol, and higher homologues: alkanolamines such as ethanolamine and N-(2-aminoethyl)ethanolamine: polyether amino alcohols such as 2-(β-aminoethoxy)ethanol; and hydroxyalkyl-substituted piperazines, such as N-(2-hydroxyethyl)piperazine, N,N'-bis(2-hydroxyethyl)piperazine, and N-(2-hydroxyethyl)bispiperazine. The difunctional alcohols are not limited to the aforementioned examples, and other equally suitable difunctional alcohols can be employed in the practice of this invention.

Preferably, the difunctional alcohols which are polyols, polyether amino alcohols, or alkanolamines are represented by the general formula:

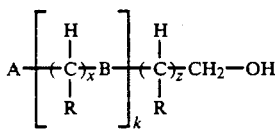

wherein A is OH or NHR; each B is independently NR or O; each R is independently hydrogen, hydroxy, amino (NH$_2$), an alkyl moiety of C$_1$–C$_{12}$ carbon atoms such as methyl, ethyl or propyl, a hydroxyalkyl or aminoalkyl moiety of C$_1$–C$_{12}$ carbon atoms, or a monocyclic aromatic moiety, such as phenyl, or tolyl; each x is independently an integer from 2 to about 12: k is an integer from 0 to about 150; and z is an integer from 1 to about 12. Preferably, each R is hydrogen. More preferably, each R is hydrogen, x is 2, and z is 1. Most preferably, each R is hydrogen, A is NH$_2$, k is 0, z is 1, and the difunctional alcohol is monoethanolamine.

In those reactions wherein the difunctional alcohol contains a piperazine moiety, the preferred difunctional alcohols are represented by the general formula:

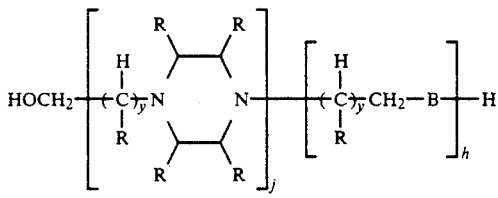

wherein each B is independently NR or O; each R is independently hydrogen, hydroxy, amino (NH$_2$), an alkyl moiety of C$_1$–C$_{12}$ carbon atoms such as methyl, ethyl or propyl, a hydroxyalkyl or aminoalkyl moiety of C$_1$–C$_{12}$ carbon atoms, or a monocyclic aromatic moiety, such as phenyl, or tolyl; each y is independently an integer from 0 to about 12; j is an integer from 1 to about 6; and h is an integer from 0 to about 6. Some examples of difunctional alcohols which satisfy this formula are N-(2-hydroxyethyl)piperazine, N-(2-hydroxyethyl)bispiperazine, N,N'-bis(2-hydroxyethyl)piperazine, and N,N'-bis(2-hydroxyethyl)bispiperazine. Preferably, each R is hydrogen. More preferably, each R is hydrogen, each y is independently 1 or 2, j is 1 or 2, h is 0, 1, or 2, and B is NR. Most preferably, each R is hydrogen, y is 1, j is 1, h is 0, and the compound is N-(2-hydroxyethyl)piperazine.

The reactant amines which are employed in the process of this invention include ammonia and any primary or secondary aliphatic amine which is capable of aminating the difunctional alcohol. Examples of suitable aliphatic amines include monoamines such as ethylamine, propylamine, n-butylamine, hexylamine, octylamine, diethylamine, dipropylamine, dibutylamine, dihexylamine, dicyclohexylamine, and dioctylamine: linear or branched alkylene diamines or polyamines such as ethylenediamine, propylenediamine, diethylenetriamine, triethylenetetramines, and tetraethylenepentamines: alkylene ether polyamines such as 2-(β-aminoethoxy)ethylamine; piperazine and mixtures of the above-identified amines. While the aforementioned amines are representative of those which are suitable in the process of this invention, other amines not recited herein may be equivalent and equally suitable.

Simple primary and secondary amines which are preferred for the process of this invention are represented by the general formula R1$_2$NH, wherein each R$^1$ is independently hydrogen or a C$_1$–C$_{12}$ alkyl moiety. Preferably, the alkylenepolyamines and alkylene ether polyamines which are suitable in the process of this invention are represented by the general formula:

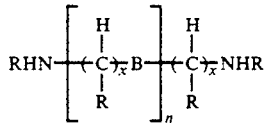

wherein each B is independently NR or O; each R is independently hydrogen, hydroxy, amino (NH$_2$), a C$_1$–C$_{12}$ *alkyl moiety such as methyl or ethyl, a* C$_1$–C$_{12}$ hydroxyalkyl or aminoalkyl moiety, or a monocyclic aromatic moiety such as phenyl or tolyl: each x is independently an integer from 2 to about 12, and n is an integer from 0 to about 150. Preferably, each B is NR and the amine is an alkylenepolyamine. More preferably, the amine is an alkylenepolyamine and each R is hydrogen. Even more preferably, each B is NR, each R is hydrogen, each x is 2, and the amine is an ethylenepolyamine. Most preferably, the amine is ethylenediamine.

In those reactions wherein the reactant amine contains a piperazine moiety, preferred piperazines or aminoalkyl-substituted piperazines are represented by the general formula:

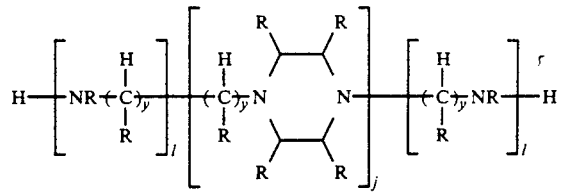

wherein each R is independently hydrogen, hydroxy, amino, an alkyl moiety of C$_1$–C$_{12}$ carbon atoms such as methyl, ethyl or propyl, a hydroxyalkyl or aminoalkyl moiety of C$_1$–C$_{12}$ carbon atoms, or a monocyclic aromatic moiety, such as phenyl, or tolyl; each y is independently an integer from 0 to about 12; each l is independently an integer from 0 to about 6: and j is an integer from 1 to about 6. Some examples of reactant amines which satisfy this formula include piperazine, N-(2-aminoethyl)piperazine, N,N'-bis(2-aminoethyl)-piperazine, bis(piperazinyl)ethane, and N-(2-aminoethyl)bispiperazine. Preferably, each R is hydrogen. More preferably, each R is hydrogen, y is 1 or 2, j is 1 or 2, and l is 0, 1, or 2. Most preferably, each R is hydrogen, y is 0, j is 1, and each l is 0, and the compound is piperazine.

In accordance with the process of this invention, any mole ratio of reactant amine to difunctional aliphatic alcohol can be used providing the amination reaction proceeds to the desired linearly-extended polyalkylenepolyamine products. Typically, the alcohol is reacted with at least about one mole equivalent of reactant amine; however, an excess of reactant amine can be advantageously employed. Preferably, the mole ratio of reactant amine to difunctional alcohol is in the range from about 0.1 to about 20. More preferably, the mole ratio of reactant amine to difunctional alcohol is in the range from about 1 to about 15: most preferably from about 2 to about 10.

Although it is preferred to carry out the amination reaction in the absence of solvent, it is within the scope of the invention for a solvent to be used, if desired. Any solvent is acceptable provided that (1) it is not reactive with the difunctional alcohol and the reactant or product amines, and (2) it does not decompose under the conditions of the reaction. Some examples of suitable solvents include water, saturated aliphatic hydrocarbons such as pentane, hexane, heptane, octane, nonane, and decane, and aromatic hydrocarbons such as benzene, toluene, and xylene. The amount of solvent employed depends upon the particular reactants and reaction conditions. Any amount of solvent is acceptable that meets the intended purpose of use. If a solvent is used, typically the solvent constitutes from about 5 weight percent to about 95 weight percent of the feed stream. Preferably, the solvent constitutes from about 10 weight percent to about 80 weight percent of the feed stream.

The catalyst employed in the process of this invention contains tungsten oxide which is essentially free of metals of Groups VIII, IB, and IIB of the Periodic Table. The term "essentially free," defined hereinbefore, means that each Group VIII, IB, or IIB metal is present in the tungsten oxide catalyst in a concentration less than about 0.1 weight percent per metal. The Groups VIII, IB, and IIB metals include iron, cobalt, nickel, ruthenium, rhodium, palladium, osmium, iridium, platinum, copper, silver, gold, zinc, cadmium, and mercury, in either the zerovalent elemental state or any ionic state. Preferably, the Group VIII, IB, and IIB metals are each present in a concentration less than about 500 ppm. More preferably, the Group VIII, IB, and IIB metals are each present in a concentration less than about 100 ppm.

The tungsten oxides which are employed in the process of this invention include binary compounds of tungsten and oxygen. These binary compounds can have an overall neutral charge, such as in $WO_2$ or $WO_3$. Alternatively, these binary compounds can be ionic salts, such as in $(NH_4)_2WO_4$. The counter cation can be any known in the art, such as hydrogen ion, ammonium ion, metallic ions, such as of Groups IA or IIA, as well as organic cations, such as tetra-butylammonium. Additionally, the tungsten oxides include compounds wherein some of the tungsten ions are replaced with vanadium, niobium, or tantalum ions, these compounds being described in detail hereinbelow. It is not within the scope of this invention for the tungsten oxides to include compounds known in the art as tungsten heteropoly acids, or their salts. The heteropoly compounds contain a framework matrix of tungsten surrounding a central heteropoly atom, such as phosphorus, silicon, or germanium. The tungsten heteropoly acids include, for example, tungstophosphoric acid and vanadotungstophosphoric acid.

The tungsten oxides employed in the process of this invention can be simple mononuclear tungsten oxides, which are compounds containing only one tungsten atom per molecular formula, such as $(NH_4)_2WO_4$. Alternatively, the tungsten oxides can be multinuclear tungsten oxide clusters, which are compounds containing a plurality of tungsten atoms per molecular formula, such as $(NH_4)_{10}(W_{12}O_{41})$. In addition, it is preferred that the tungsten be in the +4, +5, or +6 oxidation state. Examples of suitable tungsten oxides include $WO_2$, $WO_3$, $(NH_4)_2WO_4$, para-ammonium tungstate $(NH_4)_{10}(W_{12}O_{41})$, $H_2(W_6O_{19})$, $[(n-C_4H_9)_4N]_2(W_6O_{19})$, and more generally $(NR_4)_2(W_6O_{19})$ and $(NR_4)_4(W_{10}O_{32})$, wherein R is H or an alkyl moiety; however, the tungsten oxides are not limited to only the aforementioned examples. The preferred mononuclear tungsten oxide is $(NH_4)_2WO_4$. The preferred multinuclear tungsten oxide cluster compounds can be represented by the general formula:

$$C_{2+w}[M_wW_{6-w}O_{19}]$$

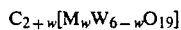

wherein C is a monovalent cation, such as $Na^+$, $K^+$, $H^+$, or a quaternary ammonium salt, $NR_4^+$, wherein R is H or an alkyl moiety such as butyl or propyl, w is an integer from 0 to 3, and M is vanadium (V), niobium (Nb), or tantalum (Ta). Preferably, C is tetrabutylammonium (+1).

The more common of the tungsten oxides, such as $WO_2$, $WO_3$, $(NH_4)_2WO_4$, and para-ammonium tungstate can be purchased commercially from Alfa Products or Aldrich. The less common oxides and cluster compounds can be prepared by methods described in *Comprehensive Inorganic Chemistry*, Vol. 3, J. C. Bailar, Jr., H. J. Emeleus, R. Nyholm, and A. F. Trotman-Dickenson, eds., Pergamon Press Ltd., Oxford, 1973, pp. 763-769; and in "Isopolytungstates," by D. L. Kepert in *Progress in Inorganic Chemistry*, Vol. 4, Intersciences Press, N.Y., 1962, p. 199. The preparation of $[(n-C_4H_9)_4N]_2(W_6O_{19})$ and various polyoxometalates is reported by M. Filowitz, R. K. C. Ho, W. G. Klemperer, and W. Shum in *Inorganic Chemistry*, 18, no.1, 93-103 (1979), and by V. W. Day, W. G. Klemperer, and C. Schwartz in the Journal of the *American Chemical Society*, 109. no. 20, 6030-6044 (1987).

The tungsten oxide catalyst can be soluble in the reaction mixture, and therefore, can act as a homogeneous catalyst. Alternatively, the tungsten oxide catalyst can be insoluble in the reaction mixture, and therefore, can act as a heterogeneous catalyst. The solubility of the tungsten oxide varies depending upon the specific alcohol and amine reactants, the size of the tungsten oxide anion, and the specific cation associated with the oxide anion. Preferably, the tungsten oxide is insoluble and acts as a heterogeneous catalyst, because then it is easier to separate from the product stream.

The tungsten oxide can be made insoluble by applying it to a support material. Any support material is acceptable provided that it does not enhance the formation of undesirable cyclic products in the process of this invention. Suitable supports include carbon and any refractory oxide such as alumina, zirconia, boria, thoria, magnesia, titania, tantala, chromia, silica, kielselguhr, niobia, zeolites, and mixtures thereof. Preferably, the support material is titania or niobia, more preferably, titania. The support material typically has a surface area of at least about 0.1 m²/g. Preferably, the support material has a surface area in the range from about 5 m²/g to about 600 m²/g; and most preferably in the range from about 50 m²/g to about 200 m²/g. These surface areas are measured by the Brunauer-Emmett-Teller (BET) method. The BET method is described by R. B. Anderson, in *Experimental Methods in Catalytic Research*, Academic Press, 1968, pp. 48-66.

The catalyst can be applied to the support material in any known fashion, such as the impregnation technique, or by precipitation in situ from the catalyst preparation reaction. Alternatively, the catalyst can be mixed with the support material, and the mixture can be heated to promote dehydration. The dehydrated composition generally comprises a catalyst which is strongly bound to the support material. This is particularly useful when the catalyst is soluble in the reaction mixture and it is desired to enhance its insolubility. Typically, from about 0.5 weight percent to about 30 weight percent tungsten is placed on the support. Preferably, the supported catalyst composition of this invention is calcined in air at a temperature not greater than about 700° C. More preferably, the calcination is conducted at a temperature in the range of 200° C. to about 400° C., most preferably, in the range from about 250° C. to about 350° C.

The amount of catalyst which is employed in the process of this invention is any amount which is effective in producing the desired linearly-extended polyalkylenepolyamine products. The amount of catalyst varies considerably depending upon the specific reactants and reaction conditions employed. Typically, in a batch reactor the amount of catalyst is in the range from about 0.1 weight percent to about 20 weight percent based on the weight of reactant amine. Preferably, the amount of catalyst is in the range from about 1 weight percent to about 15 weight percent based on the weight of reactant amine.

The process of this invention can be carried out in any suitable reactor, including batch reactors, continuous fixed-bed reactors, slurry reactors, fluidized bed reactors, and catalytic distillation reactors. Preferably, the reactor is a continuous fixed-bed reactor.

The difunctional alcohol and the amine reactants are contacted with the catalyst at any operable temperature which promotes the amination process of this invention and yields the desired linearly-extended polyalkylenepolyamine products. Typically, the temperature is in the range from about 200° C. to about 350° C. Preferably, the temperature is in the range from about 240° C. to about 325° C. More preferably, the temperature is in the range from about 260° C. to about 315° C. Below the preferred lower temperature the conversion of difunctional alcohol may be low. Above the preferred upper temperature the selectivity for linearly-extended polyalkylenepolyamines may decrease.

Likewise, the reactants are contacted with the catalyst at any operable pressure which promotes the amination process of this invention and yields the desired linearly-extended polyalkylenepolyamine products. Typically, the pressure is sufficient to maintain the reactants in the liquid state at the temperature of the reaction. Preferably, the pressure is in the range from about atmospheric to about 4000 psig. More preferably, the pressure is in the range from about 100 psig to about 3000 psig. Most preferably, the pressure is in the range from about 400 psig to about 2000 psig. In batch reactors the pressure is autogenous, and depends on the vapor pressures of the reactants and products, and upon the temperature of the reaction.

When the process of this invention is conducted in a continuous flow reactor, the flow rate of the reactants can be varied. Generally, the difunctional alcohol and the reactant amine are premixed to form a feed stream, which is fed into the reactor at any operable flow rate which yields predominantly linearly-extended polyalkylenepolyamine products. The flow rate is expressed as the liquid hourly space velocity (LHSV) and is given in units of grams of total reactants per milliliter of total reactor volume per hour, $g\ ml^{-1}\ hr^{-1}$. Preferably, the liquid hourly space velocity is in the range from about $0.1\ g\ ml^{-1}\ hr^{-1}$ to about $10.0\ g\ ml^{-1}\ hr^{-1}$; more preferably in the range from about $0.5\ g\ ml^{-1}\ hr^{-1}$ to about $4.0\ g\ ml^{-1}\ hr^{-1}$. It is understood that the space velocity controls the residence time of the reactants in the continuous flow reactor.

When the process of this invention is conducted in a batch reactor, the reaction time determines the length of contact between the reactants and the catalyst. Any reaction time is acceptable which allows for the amination reaction to proceed to the desired linearly-extended polyalkylenepolyamine products. The reaction time depends on the quantity of reactants, the quantity of catalyst, the temperature of the reaction and desired degree of conversion. Preferably, the reaction time in a batch reactor is in the range from about 1 hour to about 20 hours.

When the difunctional alcohol and the reactant amine are contacted in accordance with the process of this invention, a reaction occurs to form a polyalkylenepolyamine product. Specifically, the hydroxyl moiety of the difunctional alcohol reacts with the reactant amine to form the polyalkylenepolyamine product, and water is eliminated as a by-product. If the difunctional alcohol contains two or more hydroxyl moieties, the reactant amine may react at each hydroxyl. Preferably, the product is a mixture of polyalkylenepolyamines enriched in linearly-extended products, such as straight-chain or branched-chain adducts. For example, if the reactants are monoethanolamine and ethylenediamine, the polyalkylenepolyamine products are preferably diethylenetriamines and the straight-chain and branched tetraethylenetetramines. Similarly, if the reactants are ethylene glycol and piperazine, the preferred product is N-(2-hydroxyethyl)piperazine, which is an alcohol-extended piperazine. If the reactants are monoethanolamine and piperazine, the preferred product is N-(2-aminoethylpiperazine), which is an amine-extended piperazine. In addition to linearly-extended products, certain undesirable cyclic by-products may be formed. With reactants containing piperazine the internally cyclized product 1,4-diaza-[2.2.2]-bicyclooctane is an example of such an undesirable cyclic product. With linear reactants which do not contain piperazine, then piperazine itself is an example of such an undesirable cyclic product.

The preferred linearly-extended polyalkylenepolyamines which do not contain a piperazine moiety can be represented by the general formula:

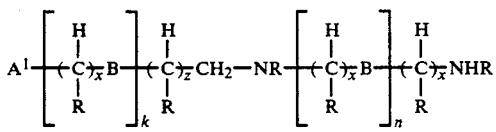

wherein each B is independently NR or O: each R is independently hydrogen, hydroxyl, amino ($NH_2$), an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl: each x is independently an integer from 2 to about 12: each n and k is independently an integer from 0 to about 150; and z is an integer from 1 to about 12: wherein $A^1$ is OH, NHR or:

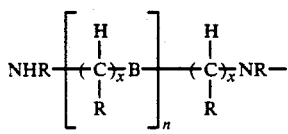

Preferably, each R is hydrogen. More preferably, each R is hydrogen, $A^1$ is $NH_2$, k is 0, y is 2, and z is 1. Most preferably, each R is hydrogen, $A^1$ is $NH_2$, k is 0, y is 2, z is 1, and n is 1, 2, or 3: thus, the polyalkylenepolyamines are diethylenetriamine, triethylenetetramine, and tetraethylenepentamine.

The preferred alcohol-extended and amine-extended piperazine products can be represented by the general formula:

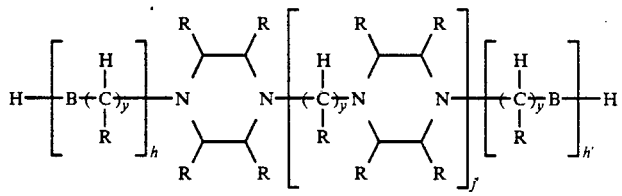

wherein each B is independently O or NR: each R is independently hydrogen, hydroxy, amino, an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl: each y is independently an integer from 0 to about 12: h and h' are each independently integers from 0 to about 6; and j' is an integer from 0 to about 6. Some examples of products which satisfy this formula include N-(2-aminoethyl)piperazine, N-(2-hydroxyethyl)-piperazine, 1,2-bis(piperazinyl)ethane (i.e. bispiperazine) and higher oligomers of piperazine. Preferably, each R is hydrogen. More preferably, each R is hydrogen, y is 1 or 2, j' is 1 or 2, h and h' are each independently 0-2, and each B is NR. Most preferably, each B is NR, each R is hydrogen, y is 2, h is 1, j' and h' are each 0, and the product is N-(2-aminoethyl)piperazine.

For the purposes of this invention, "conversion" is defined as the weight percentage of difunctional alcohol lost from the feed stream as a result of reaction. The conversion can vary widely depending upon the reactants, the form of the catalyst, and the process conditions such as temperature, pressure, and flow rate. Within the preferred temperature range, as the temperature increases the conversion generally increases. Within the preferred space velocity range, as the space velocity increases the conversion generally decreases. Typically, the conversion of the difunctional alcohol is at least about 3 weight percent. Preferably, the conversion is at least about 10 weight percent, more preferably at least about 20 weight percent, even more preferably at least about 35 weight percent, and most preferably, at least about 50 weight percent.

Likewise, for the purposes of this invention "selectivity" is defined as the weight percentage of converted difunctional alcohol which forms a particular polyalkylenepolyamine product. Typically, the selectivities also vary widely depending upon the reactants, the form of the catalyst, and the process conditions. Typically, the process of this invention achieves high selectivities to linearly-extended polyalkylenepolyamines. Within the preferred temperature range, as the temperature increases the selectivity for linearly-extended polyalkylenepolyamines generally decreases. Within the preferred space velocity range, as the space velocity increases the selectivity for linearly-extended polyalkylenepolyamines generally increases. Preferably, the combined selectivity to all linearly-extended polyalkylenepolyamines is at least about 50 weight percent: more preferably, at least about 60 weight percent: most preferably, at least about 70 weight percent.

Where applicable, the efficiency of the amination reaction in forming linearly-extended polyalkylenepolyamines is measured by the weight ratio of diethylenetriamine to piperazine, abbreviated DETA/PIP. The higher the value of this ratio, the more linearly-extended polyamines are present in the product mixture. Preferably, the DETA/PIP weight ratio is at least about 8. More preferably, the DETA/PIP weight ratio is at least about 15: most preferably, at least about 30. Another measure of the efficiency of forming linearly-extended products is the weight percentage of triethylenetetramines which are non-cyclic, %NC TETA. Preferably, %NC TETA is at least about 50 weight percent. More preferably, %NC TETA is at least about 70 weight percent: most preferably, at least about 80 weight percent.

ILLUSTRATIVE EMBODIMENTS

The following examples illustrate the invention, but are not intended to be limiting thereof. All percentages are given as weight percent, unless noted otherwise. In some instances the following abbreviations are used to indicate the reactants and products:

| | |
|---|---|
| MEA | monoethanolamine |
| EG | ethylene glycol |
| EDA | ethylenediamine |
| DETA | diethylenetriamine |
| TETA | triethylenetetramine |
| TEPA | tetraethylenepentamine |
| PIP | piperazine |
| AEEA | N-(2-aminoethyl)ethanolamine |
| AEP | N-(2-aminoethyl)piperazine |

-continued

| | |
|---|---|
| DIAEP | N,N'-bis(2-aminoethyl)piperazine |
| PEEDA | (piperazinylethyl)ethylenediamine |
| BISPIP | 1,2-bis(piperazinyl)ethane or bispiperazine |
| DABCO | 1,4-diaza-[2.2.2]-bicyclooctane |

EXAMPLE 1

(a) Preparation of Catalyst $[(n-C_4H_9)_4N]_2(W_6O_{19})$ is prepared according to the procedure described by M. Filowitz, R. K. C. Ho, W. G. Klemperer, and W. Shum in *Inorganic Chemistry*, op. cit., p. 94.

$[(n-C_4H_9)_4N]_2(W_6O_{19})$ (2.0023 g), prepared hereinabove, is dissolved in 50 ml of acetonitrile, and titania (20.0047 g; Saki, CS-200) is added to the solution. The titania is rolled in the solution while the solution is evaporated at room temperature. A dry solid, which is the titania-supported tungsten oxide catalyst, is obtained. The catalyst is dried in an oven at 200° C. overnight.

(b) Amination of Monoethanolamine

The titania-supported tungsten oxide catalyst (12.1 g), prepared in 1(a) hereinabove, is loaded into a stainless steel tubular, fixed-bed, continuous flow reactor (approximately 6 inches $\times \frac{1}{2}$ inch diameter) fitted with glass wool plugs. A mixture of monoethanolamine and ethylenediamine in an EDA/MEA mole ratio of 2/1 is passed through the catalyst bed at a variety of reaction temperatures, pressures, and flow rates. The liquid effluent from the reactor is collected and sampled by gas phase chromatography. A CAM (Carbowax amine deactivated) capillary column (30 m×0.25 mm dia.) is employed to measure total amine products. Isomer distributions are measured on an SE-30 capillary column (30 m×0.25 mm dia.). An SE-54 capillary column (30 m×0.25 mm dia.) is also used in analyzing for total amine content and isomer distribution. The process conditions and results are presented in Table I.

It is seen that monoethanolamine is aminated with ethylenediamine in the presence of a catalyst containing a titania-supported tungsten oxide cluster. It is also seen from the DETA/PIP weight ratio and %NC TETA that the products are predominantly linearly-extended, non-cyclic polyethylenepolyamines.

EXAMPLE 2

(a) Preparation of Catalyst $[(n-C_4H_9)_4N]_3(VW_5O_{19})$ is synthesized in the manner described by M. Filowitz, R. K. C. Ho, W. G. Klemperer, and W. Shum in *Inorganic Chemistry*, op. cit., p. 94.

The $[(n-C_4H_9)_4N]_3(VW_5O_{19})$ (2.0074 g), prepared hereinabove, is dissolved in 50 ml of acetonitrile, and titania (20.0575 g: Saki, CS-200) is added to the solution. The titania is rolled in the solution while the solution is evaporated at room temperature. A dry solid is obtained and dried in an oven at 200° C. overnight. The dried solid is the titania-supported vanadium-tungsten oxide catalyst.

(b) Amination of Monoethanolamine

The titania-supported catalyst (12.4g), prepared in 2(a) hereinabove, is loaded into the reactor of Example 1, and the amination of monoethanolamine with ethylenediamine is conducted as in Example 1 with the results shown in Table I. It is seen that monoethanolamine is aminated with ethylenediamine in the presence of a titania-supported vanadium-tungsten oxide catalyst to predominantly linearly-extended, non-cyclic polyethylenepolyamines.

EXAMPLE 3

(a) Preparation of Catalyst

Para-ammonium tungstate (15.0 g; Amends Chemical Company) is dissolved in about 400 ml of water containing 5 ml of 30 percent hydrogen peroxide by heating at 80°–90° C. for about 1 hour. The solution is cooled to room temperature and added to a flask containing titania (25.0 g; Saki CS 200, 20–35 mesh). The water is removed from the resulting mixture by rotary evaporation to yield a dried solid. The dried solid is further dried in a muffle furnace at 300° C. over the weekend to yield the titania-supported ammonium tungstate catalyst.

TABLE I

| | | | | | % Selectivity (EDA-MEA and water free basis) | | | | | | |
|---|---|---|---|---|---|---|---|---|---|---|---|
| Ex. | Temp. °C. | Pres. psig | LHSV g ml$^{-1}$ hr$^{-1}$ | % MEA Conversion | DETA | TETA (% NC TETA) | TEPA | PIP | AEP | AEEA | DETA/ PIP |
| 1a | 301 | 1422 | 0.73 | 25.9 | 67.3 | 12.4 (99.5) | 3.54 | 0.90 | 1.47 | 14.4 | 74.9 |
| 1b | 302 | 1416 | 1.00 | 33.8 | 65.5 | 13.8 (99.5) | 4.86 | 0.98 | 1.45 | 13.4 | 66.8 |
| 1c | 310 | 1434 | 0.49 | 52.1 | 58.0 | 18.4 (94.0) | 11.0 | 1.59 | 2.13 | 8.78 | 36.5 |
| 1d | 318 | 1428 | 0.60 | 64.7 | 50.0 | 20.2 (91.3) | 18.7 | 2.88 | 2.69 | 5.58 | 17.3 |
| 2a | 310 | 1422 | 0.60 | 45.2 | 64.6 | 14.0 (~100) | 3.7 | 1.3 | 1.9 | 14.6 | 49.7 |
| 2b | 316 | 1422 | 0.52 | 54.2 | 73.4 | 6.7 (86.2) | 6.7 | 3.4 | 5.6 | 4.1 | 21.6 |
| 3a | 310 | 1428 | 0.76 | 58 | 60 | 20 (99) | 7 | 2 | 2 | 8 | 26 |
| 3b | 305 | 1422 | 0.72 | 46 | 66 | 15 (99) | 5 | 2 | 1 | 10 | 39 |

(b) Amination of Monoethanolamine

The catalyst (17.0 g), prepared in 3(a) hereinabove, is used in the fixed-bed continuous flow reactor of Example 1. A mixture of ethylenediamine and monoethanolamine in a mole ratio of 2:1 is passed through the catalyst bed with the results shown in Table I. It is seen that passed over the catalyst at a variety of process conditions with the results shown in Table II.

TABLE II[1]

| EX. 5 | Temp. (°C.) | P (psig) | LHSV g ml$^{-1}$ hr$^{-1}$ | % MEA Conv. | Selectivity[2] | | | | | | |
|---|---|---|---|---|---|---|---|---|---|---|---|
| | | | | | AEEA | AEP | Linear TETA | DIAEP | PEEDA | BISPIP | OTHER[3] |
| b-1 | 300 | 1400 | 0.88 | 51.9 | — | 64.8 | — | 8.9 | 13.7 | 4.1 | 8.5 |
| b-2 | 300 | 1400 | 0.88 | 56.7 | 6.7 | 51.6 | 7.2 | 6.7 | 9.1 | 1.2 | 17.4 |
| b-3 | 310 | 1400 | 0.88 | 63.2 | 4.5 | 51.5 | — | 7.8 | 8.9 | 1.2 | 26.0 |
| b-4 | 310 | 525 | 0.88 | 79.8 | — | 44.1 | — | 10.8 | 7.0 | — | 38.1 |
| b-5 | 310 | 1000 | 0.44 | 89.5 | — | 43.9 | — | 11.6 | 9.3 | 2.3 | 33.0 |

[1]The feedstream comprises 7.2% EDA, 30.3% MEA, 53.8% PIP, and 7.7% DETA, based on area percentages of the organic components as analyzed by gas chromotography. The MEA/PIP mole ratio is 1.3:1. Additionally, the feed contains 18-20 weight percent water.
[2]Calculated on feed-free and H$_2$O-free basis from GC area percentages corrected for individual response factors.
[3]Other products included branched TETA, linear and branched TEPA, higher piperazinyl homologs, and traces of EDA.

monoethanolamine is aminated with ethylenediamine in the presence of a catalyst of titania-supported para-ammonium tungstate. The products are predominantly linearly-extended and non-cyclic polyethylenepolyamines.

EXAMPLE 4

(a) Preparation of Catalyst

Para-ammonium tungstate (15.0 g; Amends Chemical Company) is dissolved in about 400 ml of water containing 5 ml of 30 percent hydrogen peroxide by heating at 80°-90° C. for about 1 hour. The solution is cooled to room temperature and added to a flask containing silica (25.0 g; Shell silica spheres S-980 G 1.5 mm). The water is removed from the resulting mixture by rotary evaporation to yield a dried solid. The dried solid is heated in a muffle furnace at 350° C. overnight to yield a silica-supported ammonium tungstate catalyst.

(b) Amination of Monoethanolamine

The catalyst (7.90 g), prepared in 4(a) hereinabove, is placed in the fixed-bed continuous flow reactor of Example 1. A mixture of ethylenediamine and monoethanolamine in a mole ratio of 2:1 is passed over the catalyst at a temperature of 290° C., a pressure of 1405 psig, and a liquid hourly space velocity of 0.88 g ml$-1$ hr$-1$. The following results are obtained: conversion of MEA, 21 percent; selectivities to DETA, 51 percent: TETA, 19 percent: TEPA, 6 percent; PIP, 5 percent; AEP, 5 percent: and AEEA, 14 percent. The DETA/PIP ratio is 9, and the % NC TETA is 87 percent. It is seen that monoethanolamine is aminated with ethylenediamine in the presence of a silica-supported tungsten oxide catalyst to predominantly linearly-extended and non-cyclic polyethylenepolyamines.

EXAMPLE 5

(a) Preparation of Catalyst

Titania (TiO$_2$ Saki Cs 200: 44.0 g, 14–20 mesh) is combined in a 1 liter round bottom flask with a solution comprising para-ammonium tungstate (6.0 g) dissolved in 600 ml of water. The water is slowly removed on a rotary evaporator to yield a dry solid. The dry solid is heated to 350° C. in a furnace under air for 24 hours to yield a catalyst comprising para-ammonium tungstate supported on titania.

(b) Amination of Monoethanolamine

The catalyst (20 g), prepared in 5(a) hereinabove, is placed in the fixed-bed continuous flow reactor of Example 1. A feed comprising monoethanolamine and piperazine and having a MEA/PIP mole ratio of 1.3:1 is passed over the catalyst at a variety of process conditions with the results shown in Table II.

It is seen that monoethanolamine is aminated by piperazine in the presence of a titania-supported tungsten oxide catalyst to predominantly aminoethylpiperazine and other higher linearly-extended polyethylenepolypiperazines.

EXAMPLE 6

(a) Preparation of Catalyst

Para-ammonium tungstate (14.0g) is dissolved in 400 ml of water to which 5 ml of 30 weight percent hydrogen peroxide is added. The resulting solution is heated to between 80° C. and 90° C. Niobic acid (19.0 g: Niobium Products Corp., CBMM number 222) is pressed at 20,000 psig into cylindrical pellets 1 inch in diameter by 1 inch in height. The pellets are crushed and sieved to 14-20 mesh, then added to the heated solution. The resulting mixture is rolled while the water is removed by rotary evaporation to yield a dried solid. The dried solid is further dried in a muffle furnace at 300° C. overnight to yield a niobia-supported tungsten oxide catalyst.

(b) The catalyst (26.0g), prepared in 6(a) hereinabove, is loaded into the reactor of Example 1. Monoethanolamine and diethylenetriamine in an MEA/DETA mole ratio of 2/1 is passed over the catalyst at 260° C., 1416 psig, and a LHSV of 2.88 g ml$-1$ hr$-1$. At an MEA conversion of 40 percent the selectivities in the product mixture are the following: EDA, 14 percent: TETA, 36 percent; TEPA, 25 percent: PIP, 3 percent: AEP, 6.6 percent; AEEA, 8.5 percent; and higher oligomers, 10 percent. The TETA fraction is found to contain 85 percent non-cyclics. It is seen that the niobia-supported tungstate catalyst catalyzes the amination of monoethanolamine with diethylenetriamine to predominantly linearly-extended and non-cyclic polyethylenepolyamines.

What is claimed is:

1. A process for preparing linearly-extended polyalkylenepolyamines comprising contacting a difunctional aliphatic alcohol with a reactant amine in the presence of tungsten oxide catalyst under conditions such that a mixture of polyalkylenepolyamines enriched in linearly-extended products is produced; wherein said tungsten oxide catalyst is a binary compound of tungsten and oxygen, or a salt thereof, or a compound obtained from a binary compound of tungsten and oxygen by replacing a portion of the tungsten atoms with vanadium, niobium or tantalum; and wherein said tungsten oxide catalyst is essentially free of the metals of Groups VIII, IB, and IIB.

2. The process of claim 1 wherein the difunctional alcohol is represented by the formula:

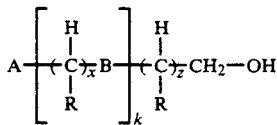

wherein A is OH or NHR; each B is independently NR or O; each R is independently hydrogen, hydroxyl, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety: x is an integer from 2 to about 12: k is an integer from 0 to about 150: and z is an integer from 1 to about 12.

3. The process of claim 2 wherein each R is hydrogen.

4. The process of claim 3 wherein x is 2 and z is 1.

5. The process of claim 4 wherein each R is hydrogen, A is NH$_2$, k is 0, z is 1, and the difunctional aliphatic alcohol is monoethanolamine.

6. The process of claim 1 wherein the difunctional alcohol is represented by the following formula:

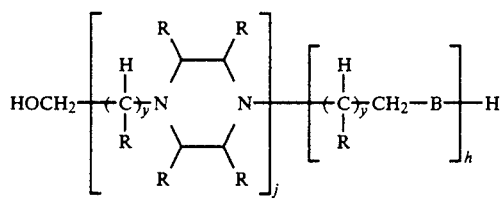

wherein each B is independently NR or 0; each R is independently hydrogen, hydroxy, amino (NH$_2$), an alkyl moiety of $C_1$-$C_{12}$ carbon atoms, a hydroxyalkyl or aminoalkyl moiety of $C_1$-$C_{12}$ carbon atoms, or a monocyclic aromatic moiety: each y is independently an integer from 0 to about 12; j is an integer from 1 to about 6: and h is an integer from 0 to about 6.

7. The process of claim 1 wherein the reactant amine is represented by the formula:

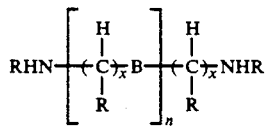

wherein each B is independently NR or 0; each R is independently hydrogen, hydroxyl, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety; each x is independently an integer from 2 to about 12, and n is an integer from 0 to about 150.

8. The process of claim 7 wherein each B is NR.

9. The process of claim 8 wherein the amine is an ethylenepolyamine.

10. The process of claim 1 wherein the reactant amine is represented by the formula:

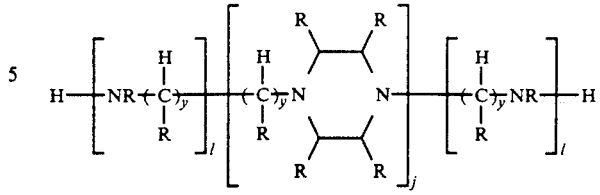

wherein each R is independently hydrogen, hydroxy, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety: each y is independently an integer from 0 to about 12; each l is independently an integer from 0 to about 6; and j is an integer from 1 to about 6.

11. The process of claim 10 wherein each R is hydrogen, y is 0, j is 1, and each l is 0, and the reactant amine is piperazine.

12. The process of claim 1 wherein the mole ratio of reactant amine to difunctional aliphatic alcohol is at least about 1.

13. The process of claim 1 wherein each of the Group VIII, IB, or IIB metals is present in the catalyst in a concentration less than about 500 ppm.

14. The process of claim 13 wherein each of the Group VIII, IB, or IIB metals is present in the catalyst in a concentration less than about 100 ppm.

15. The process of claim 1 wherein the catalyst is a mononuclear tungsten oxide.

16. The process of claim 15 wherein the catalyst is (NH$_4$)$_2$WO$_4$.

17. The process of claim 1 wherein the catalyst is a multinuclear tungsten oxide cluster having the formula:

wherein C is a monovalent cation, w is an integer from 0 to 3, and M is V, Nb, or Ta.

18. The process of claim 1 wherein the amount of catalyst is in the range from about 0.1 weight percent to about 20 weight percent based on the weight of reactant amine.

19. The process of claim 1 wherein the temperature is in the range from about 200° C. to about 350° C.

20. The process of claim 1 wherein the pressure is in the range from about atmospheric to about 4000 psig.

21. The process of claim 1 wherein the liquid hourly space velocity is in the range from about 0.1 g ml$^{-1}$ hr$^{-1}$ to about 10.0 g ml$^{-1}$ hr$^{-1}$.

22. The process of claim 1 wherein the linearly-extended polyalkylenepolyamines are represented by the formula:

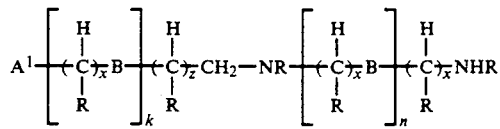

wherein each B is independently NR or 0, each R is independently hydrogen, hydroxyl, amino, an alkyl moiety of $C_1$-$C_{12}$ carbon atoms, a hydroxyalkyl or amino alkyl moiety of $C_1$-$C_{12}$ carbon atoms, or a monocyclic aromatic moiety; each x is independently an integer from 2 to about 12: z is an integer from 1 to about 12:

k and n are each integers from 1 to about 150: and wherein $A^1$ is OH, NHR or:

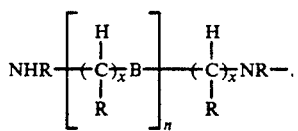

23. The process of claim 22 wherein each R is hydrogen.
24. The process of claim 23 wherein $A^1$ is $NH_2$, k is 0, y is 2, and z is 1.
25. The process of claim 1 wherein the polyalkylenepolyamine product is an alcohol-extended or amine-extended piperazine which is represented by the general formula:

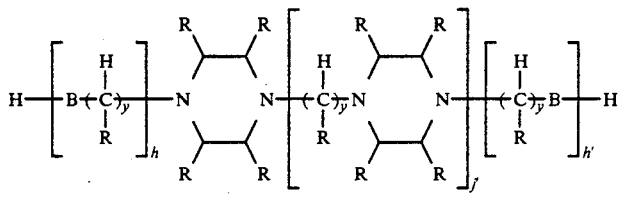

wherein each B is independently 0 or NR; each R is independently hydrogen, hydroxy, amino, an alkyl moiety of $C_1$-$C_{12}$ carbon atoms, a hydroxyalkyl or aminoalkyl moiety of $C_1$-$C_{12}$ carbon atoms; each y is independently an integer from 0 to about 12; h and h' are each independently integers from 0 to about 6: and j' is an integer from 0 to about 6.
26. The process of claim 25 wherein each B is NR, each R is hydrogen, y is 2, h is 1, j' and h' are each 0, and the compound N-(2-aminoethyl)piperazine.
27. A process for preparing non-cyclic polyethylenepolyamines comprising contacting monoethanolamine with ethylenediamine in the presence of a supported tungsten oxide catalyst at a temperature in the range from about 200° C. to about 350° C., a pressure in the range from about 100 psig to about 3000 psig, and a liquid hourly space velocity in the range from about 0.1 g ml$^{-1}$ hr$^{-1}$ to about 10.9 g ml$^{-1}$ hr$^{-1}$ such that a mixture of polyethylenepolyamines enriched in linearly-extended products is formed, wherein said catalyst is a supported binary compound of tungsten and oxygen, or a salt thereof, or a supported compound obtained from a binary compound of tungsten and oxygen by replacing a portion of the tungsten atoms with vanadium, niobium or tantalum; and wherein said tungsten oxide catalyst is essentially free of the metals of Groups VIII, IB, and IIB.
28. The process of claim 27 wherein the DETA/PIP mole ratio is at least about 15.
29. The process of claim 27 wherein the percentage of triethylenetetramines which is non-cyclic is at least about 70 weight percent.
30. The process of claim 27 wherein the DETA/PIP mole ratio is at least about 30.
31. The process of claim 30 wherein the percentage of triethylenetetramines which is non-cyclic is at least about 80 weight percent.
32. A process for preparing linearly-extended polyalkylenepolyamines comprising contacting a difunctional aliphatic alcohol with a reactant amine in the presence of a catalyst under conditions such that a mixture of polyalkylenepolyamines enriched in linearly-extended products is produced; said catalyst being a multinuclear tungsten oxide cluster having the formula:

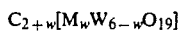

wherein C is the monovalent cation (n-$C_4H_9$)$_4$N, and w is the integer 0 or 1, and M is V, such that the catalyst is [(n-$C_4H_9$)$_4$N]$_2$W$_6$O$_{19}$ or [(n-$C_4H_9$)$_4$N]$_3$(VW$_5$O$_{19}$), and such that said multinuclear tungsten oxide cluster is essentially free of the metals of Groups VIII, IB, and IIB.
33. The process of claim 1 wherein the catalyst is para-ammonium tungstate represented by the formula (NH$_4$)$_{10}$(W$_{12}$O$_{41}$).

* * * * *